United States Patent [19]

Chromecek et al.

[11] Patent Number: 4,962,170

[45] Date of Patent: Oct. 9, 1990

[54] METHOD OF MAKING HIGHLY ABSORPTIVE POLYMERS

[75] Inventors: Richard C. Chromecek, Litchfield County, Conn.; Milan F. Sojka, Orange County, N.Y.; Lon L. Weiss, Fresno County, Calif.

[73] Assignee: Dow Corning Corporation, Midland, Mich.

[21] Appl. No.: 401,582

[22] Filed: Aug. 31, 1989

[51] Int. Cl.$^5$ .................................................. C08F 2/06
[52] U.S. Cl. .................................... 526/212; 526/323.1
[58] Field of Search ............... 526/212, 238.21, 318.1, 526/320, 336, 321, 323.1

[56] References Cited

U.S. PATENT DOCUMENTS

| | | | |
|---|---|---|---|
| Re. 27,026 | 1/1971 | Alfrey, Jr. et al. | 521/147 |
| 2,809,943 | 10/1957 | Pye et al. | 521/28 |
| 3,418,262 | 12/1968 | Werotte et al. | 521/32 |
| 3,509,078 | 4/1970 | Roubinek et al. | 521/62 |
| 3,575,946 | 4/1971 | Chromecek et al. | 526/212 |
| 3,583,957 | 6/1971 | Chromecek et al. | 526/320 |
| 3,627,770 | 12/1971 | Morse | 521/63 |
| 3,637,535 | 1/1972 | Corte et al. | 521/32 |
| 3,767,600 | 10/1973 | Albright | 521/29 |
| 3,815,239 | 6/1974 | Lee, Jr. et al. | 526/321 |
| 3,989,649 | 11/1976 | Kaibo et al. | 521/29 |
| 4,076,921 | 2/1978 | Stol et al. | 526/320 |
| 4,208,309 | 6/1980 | Kraemer et al. | 521/53 |
| 4,224,415 | 9/1980 | Meitzner et al. | 521/38 |
| 4,414,278 | 11/1983 | Cohen et al. | 526/323.1 |
| 4,515,931 | 5/1985 | Olson et al. | 526/323.1 |
| 4,655,957 | 4/1987 | Chromecek et al. | 252/174.23 |
| 4,661,327 | 4/1987 | Horton | 423/7 |
| 4,690,825 | 9/1987 | Won | 424/501 |
| 4,724,240 | 2/1988 | Abrutyn | 514/401 |
| 4,806,360 | 2/1989 | Leong et al. | 424/487 |
| 4,833,198 | 5/1989 | Stanley, Jr. et al. | 526/207 |

FOREIGN PATENT DOCUMENTS

| | | |
|---|---|---|
| 1168157 | 5/1984 | Canada. |
| 252463 | 1/1988 | European Pat. Off. . |
| 2608533 | 9/1976 | Fed. Rep. of Germany . |
| 88/1164 | 2/1988 | PCT Int'l Appl. . |

*Primary Examiner*—Joseph L. Schofer
*Assistant Examiner*—R. H. Delmendo
*Attorney, Agent, or Firm*—Susan M. Cornwall

[57] ABSTRACT

A method of forming a highly adsorptive polymer, which includes the steps of: (a) homogeneously mixing a solution of a monomer consisting exclusively of one or more types of polyunsaturated monomer, a monomer solvent, and an initiator, (b) polymerizing the monomers to form a polymer, wherein the monomer solvent is a solvent for the monomers and a non-swelling non-solvent for the polymer, and (c) removing the solvent from the polymer to form a dry powder.

8 Claims, No Drawings

METHOD OF MAKING HIGHLY ABSORPTIVE POLYMERS

BACKGROUND OF THE INVENTION

The invention relates to a method of making highly adsorptive polymers, specifically by polymerization of monomers by the precipitation polymerization technique.

In the art of making polymeric particles capable of entrapping fluids and/or solids (actives), there exists a few different techniques that are usually used. One such technique entails polymerization in the presence of actives giving monolithic articles where the actives stay in the monolithic article (in situ polymerization) or are extracted, leaving macroporous cross-linked polymeric structures. In the latter case, the actives, since they are forming pores, are sometimes called porogens. After extraction, the rigid porous polymer can be refilled by other actives. The porogen is soluble in the monomers, but does not swell the resulting polymer. Dependent on the physical properties of the porogen, the formation of the macropores can be achieved by proper (increased) cross-linking.

A very convenient method of preparation of both of these systems is suspension polymerization in a medium (solvent) which does not dissolve the monomers and actives. Usually for hydrophobic systems, the solvent is water, and for hydrophilic systems, the solvent is cyclohexane, benzene, toluene, xylene, chlorobenzenes, chloroethanes, etc. Protective colloids such as polyvinylpyrolidone, polyvinylalcohol, magnesium hydroxide, calcium phosphate, etc. are used to prevent the coalescence of the beads during polymerization.

Both of the above mentioned systems are "in situ polymerization" techniques, using the same principle in that the polymerization is carried out in the presence of the active or porogen. The only difference between these systems is that, in the case of the actives, the product is used as such, while in the case of the porogen, the porogen is usually extracted and replaced by another material. The procedure of extracting and replacing is very often tedious, adding cost to the manufacturing.

In situ polymerization is carried out by dissolving the monomers in a functional material to form a uniform solution, and, thereafter, inducing polymerization. The functional material must be a solvent for the monomers, but not a swelling agent for the polymer. The resulting product of in situ polymerization is a solid material formed of a polymeric lattice entrapping the functional material. The amount of functional material used is such that when polymerization is complete, the functional material is substantially wholly contained within the polymeric lattice and does not exist freely in the product. If the functional material is extracted from the polymeric lattice, the resulting polymer is in the form of hard, porous beads.

The third method of making polymers capable of entrapping other materials is by precipitation polymerization. The resulting product from precipitation polymerization is generally a polymer in the form of a powder and the powder is a combined system of particles. The system of powder particles includes unit particles, agglomerates of fused unit particles, and aggregates of clusters of fused agglomerates. The particles themselves are not generally highly porous. This invention describes an improved method for making such powders using precipitation polymerization.

As described, the type of polymerization technique used is an important factor in the determination of the resulting product. In addition, within each type of polymerization, there are procedural alternatives which, too, can have a significant impact on the resulting product. The differences in the polymerization techniques are enough that a procedure used in one type of polymerization technique will not necessarily have the same effect if used in another polymerization technique. Therefore, techniques and procedures are carefully selected based on the product properties desired.

With respect to the prior art, however, there remains a need for an easy, consistent method of making submicron size, highly adsorptive, powder-type polymers which are of a soft nature suitable for cleaning scratchable surfaces, such as contact lenses.

SUMMARY OF THE INVENTION

The method invention provides a solution for the above-mentioned need. Specifically, the invention is a method of forming a highly adsorptive polymer, comprising the steps of: (a) homogeneously mixing a solution comprising from 0.1 parts by weight to less than 25 parts by weight of a monomer consisting exclusively of one or more types of polyunsaturated monomer, from greater than 75 parts by weight up to 99.9 parts by weight of a monomer solvent, wherein the total weight of the monomers and the monomer solvent is 100 parts, and 0.05 to 5 weight percent initiator based on the weight of said monomer, and (b) polymerizing the monomers to form a polymer, wherein the monomer solvent is a solvent for the monomers and a non-swelling non-solvent for the polymer. The method has the advantage of being simpler than prior art methods when only one monomer type is polymerized, because this results in a reduction of measuring steps required and reduces the variability of the product by reducing chances for error in measuring the ingredients. The resulting polymer can adsorb large quantities of various substances, having different structures and properties.

DETAILED DESCRIPTION OF PREFERRED EMBODIMENTS OF THE INVENTION

The highly crosslinked polymeric systems of this invention are prepared by polymerizing monomers having at least two unsaturated bonds (hereinafter referred to as "polyunsaturated" monomers) and containing no comonomers having monounsaturated moiety. Examples of this group of monomers can be poly-acrylates ("poly" meaning two or more), -methacrylates, or -itaconates of: ethylene glycol, propylene glycol; di-, tri-, tetra-, or poly-ethylene glycol and propylene glycol; trimethylol propane, glycerine, erythritol, xylitol, penta erythritol, di penta erythritol, sorbitol, mannitol, glucose, sucrose, cellulose, hydroxyl cellulose, methyl cellulose, 1,2 or 1,3 propanediol, 1,3 or 1,4 butanediol, 1,6 hexanediol, 1,8 octanediol, cyclohexanediol, or cyclohexanetriol. Similarly, bis(acrylamido or methacrylamido) compounds can be used. These compounds are, for example, methylene bis(acryl or methacryl)amide, 1,2 dihydroxy ethylene bis(acryl or methacryl)amide, hexamethylene bis(acryl or methacryl)amide. Another group of valuable monomers could be represented by di or poly vinyl esters such as divinyl-oxalate, -malonate, -succinate, -glutamate, -adipate, -sebacate, -maleate, -fumarate, -citraconate, and mesaconate.

Still another group of monomers is represented by di or poly vinyl ethers of ethylene, propylene, butylene, etc., glycols, glycerine, penta erythritol, sorbitol, di or poly allyl compounds such as those based on glycols, glycerine, etc., or combinations of vinyl allyl or vinyl acryloyl compounds such as vinyl methacrylate, vinyl acrylate, allyl methacrylate, allyl acrylate, methallyl methacrylate, or methallyl acrylate. In addition, aromatic, cycloaliphatic and heterocyclic compounds are suitable for this invention. These compounds include divinyl benzene, divinyl toluene, divinyl diphenyl, divinyl cyclohexane, trivinyl benzene, divinyl pyridine, and divinyl piperidine. Furthermore, divinyl ethylene or divinyl propylene urea and similar compounds may be used, e.g., as described in U.S. Pat. Nos. 3,759,880, 3,992,562, and 4,013,825, which are hereby incorporated by reference. Acryloyl- or methacryloyl-endcapped siloxane and polysiloxanes such as those described in U.S. Pat. Nos. 4,276,402, 4,341,889, French Patent No. 2,465,236, and German Publication GER OLS Patent No. 3,034,505, which are hereby incorporated by reference, are suitable for this invention. Methacryloyl-endcapped urethanes, such as those described in U.S. Pat. Nos. 4,224,427, 4,250,322, and 4,423,099, German Publications GER OLS No. 2,365,631 and 2,542,314, Japanese Patent Application Nos. 85/233,110, 86/09,424, and 86/30,566, and British Patent No. 1,443,715, are suitable for this invention. Urethane acrylates of polysiloxane alcohols as described in U.S. Pat. Nos. 4,543,398 and 4,136,250 and bisphenol A bis methacrylate and ethoxylated bisphenol A bis methacrylate are also suitable monomers for this invention.

It should be understood that one type or mixtures of two or more types of the above-mentioned monomers can be used in this invention. The types of monomers used may be selected according to the adsorption properties desired. The chemical structure and adsorption property can be adjusted via changing the structure of the chain between the unsaturated bonds. For example, if the monomer includes a saturated hydrocarbon structure like 1,4 butanediol bis methacrylate, the adsorptivity of the powder will be shifted more to the hydrophobic side, while tetraethylene glycol bis methacrylate, having —$CH_2CH_2O$— units in its connecting chain will impart a more hydrophilic character.

The polymerization is simply done by dissolving the monomers or their mixtures in a solvent which does not swell or dissolve the resulting polymer. Based on the parts by weight of the monomer and the solvent totalling 100 parts by weight, the monomers are used from 0.1 to less than 25 parts by weight, preferably, from 2 to less than 25 parts by weight, and, more preferably, from 5 to 20 parts by weight. Correspondingly, the solvent is present from greater than 75 parts by weight to 99.9 parts by weight, preferably, from greater than 75 parts by weight to 98 parts by weight, and, most preferably, from 80 parts by weight to 95 parts by weight. No surfactant or dispersing aid is required. In the majority of cases, alcohols can be used as the monomer solvent. It is important that the solvent does not swell the polymer, or the polymer will become hard upon drying. Swelling is considered to be evidenced by an increase in volume or by dilation. The amount of swelling that is considered excessive or detrimental depends on the polymer. Detrimental swelling causes the gluing of unit particles together, resulting finally in a clear gel.

For example, when isopropyl alcohol is used as the monomer solvent when making a polymer from tetraethylene-glycol dimethacrylate, it was surprisingly found that the isopropyl alcohol must be anhydrous or the water/isopropyl alcohol cosolvent will swell the poly(tetraethylene glycol methacrylate), causing the polymer to be hard upon drying. For this invention, swelling is determined to be minimal (thus, acceptable) when submicron particles are obtained. On the other hand, if the particles after drying are glued together, forming a hard mass, there is considered limited swelling. Preferably the solvent is relatively volatile, having a boiling point of less than 80° C. at one atmosphere and is water-miscible. The method of this invention is further simplified from many prior art methods in that the removal of the solvent is done simply by filtration and evaporation, e.g. by heat and/or vacuum. In the specific case of making poly(tetraethylene glycol methacrylate) with isopropyl alcohol, it was found that the drying had to be done under anhydrous conditions, or the polymer would become hard upon drying. By anhydrous conditions, it is generally meant that humidity during drying be less than 40% relative humidity. Generally, no solvent extraction is required. The polymer can be washed with a suitable solvent, e.g. the same solvent used in polymerization, before it is dried.

The polymerization is achieved by using one of a variety of free radical initiators which can be, among others, an azo compound, a peroxy dicarbonate, a peroxy ester, or a sulfonyl acid peroxide. Preferably, the free radical initiator will have a 10-hour half life temperature of 75° C. or less, i.e. it is a low to medium temperature initiator. The initiator is employed in an amount from 0.05 to 5 weight percent of the total monomer charge.

Preferably, the initiators of this invention are redox initiators, preferably, secondary or tertiary amines and, more preferably, a tertiary amine and peroxide combination. The ratio between the peroxide and the amine may vary from 0.1 to 5 moles. It is useful to first dissolve the peroxide in a part of the solvent, and separately dissolve the amine in the other part of the solvent, then mix the peroxide part with the monomer solution at room temperature and, subsequently, add the amine part. The charging of the peroxide and amine part can be done at the beginning of the reaction or in portions throughout the reaction period. These amines are generally of the formula $R_2NH$ or $R_3N$ wherein R is an alkyl or substituted alkyl, cycloalkyl, or aryl group. Preferably the amine is a tertiary amine.

Illustrative redox initiators of this invention are methylbutyl amine, bis(2-hydroxyethyl)butyl amine, butyldimethyl amine, dimethyl amine, dibenzylethyl amine, diethylmethyl amine, dimethylpentyl amine, diethyl amine, 2,2',2''-trihydroxy dipropyl ethyl amine, di-n-propylene amine, 2,2',2''-trimethyl tributyl amine, triethyl amine, dimethyl aminoacetal, pentylhexyl amine, triethanolamine, trihexyl amine, trimethyl amine, trioctadecyl amine, tripropyl amine, trisopropyl amine, tetramethylene diamine, and esters of para-amino benzoic acid, e.g., p-dimethyl amino-2-ethylhexyl-benzoate, dimethyl aminoethyl acetate, 2-(n-butoxy)ethyl 4-dimethylaminobenzoate, 2-(dimethylamino) ethyl benzoate, ethyl-4dimethylaminobenzoate, methyldiethanolamine, dibutyl amine, N,N-dimethylbenzylamine, methylethyl amine, dipentyl amine and peroxide $Fe^{2+}$.

Other preferred initiators are selected from inorganic initiators such as sodium, potassium, or ammonium persulfates, as the decomposition products of such bisulfates is less harmful than many decomposition products of organic initiators.

The reaction is carried out in the presence of an inert atmosphere. This condition may be achieved by the use of nitrogen, argon, carbon dioxide and the like. Usually, no stirring or very slow stirring (e.g. zero to 300 rotations per minute) is employed.

The reaction is maintained for such time as is required to achieve the desired yield of polymer. This time may be as little as one half hour. However, to approach the theoretical yield, 24 to 48 hours at room temperature, or 4 to 10 hours at elevated temperatures, are required. The monomer solvent is subsequently removed by filtration and evaporation, resulting in a dry powder, which can be post adsorbed with a variety of functional active ingredients.

As mentioned, the polymer is in the form of a powder and not hard spheres or beads. The powder is a combined system of particles. The system of particles includes submicron unit particles ranging in size from 0.1 to 0.5 microns in diameter. The particles may range from elliptical to spherical in shape. A typical diameter of a particle is about 0.3 microns. The powder also consists of agglomerates of fused unit particles of sizes in the range of about ten to eighty microns in average diameter, and aggregates of clusters of fused agglomerates of sizes in the range of about two hundred to about eight hundred microns in average diameter. When mild pressure is applied to the powder, the aggregates and agglomerates are easily crushed into the small particles. Thus, the powder can be described as being "soft" in that the aggregate and agglomerate structure easily changes upon pressure and they cannot be easily felt when rubbed on the skin, between teeth, or on sensitive human mucous membranes. The powders disappear when rubbed upon a surface. This phenomenon is believed to be due to the fact that large aggregates of the material scatter light rendering the appearance of a white particulate; however, upon rubbing, these large aggregates decrease in size approaching the range of visible light and, hence, seem to disappear. The materials do not swell in common solvents and are capable of physically adsorbing active ingredients by filling of interstitial voids by capillary action. The powders are often capable of adsorbing from sixty to eighty percent of a liquid and yet remain free flowing. The unit particles themselves do not have any significant porosity, usually less than 2%.

The size and adsorptive properties of these polymeric particles can be influenced by the concentration of the monomers and stirring rate. As a matter of rule, lower concentrations of the monomers and slower stirring result in higher adsorptivity.

The powder produced by this invention exhibits adsorbent and abrasive properties which make them useful both as cleaning agents and as delivery systems. The powder has great cleaning ability when employed as an abrasive in cleaners without the scratching, grinding, gouging, etc., which is objectionable during cleaning optical surfaces and other fine surfaces. The nature of the powder permits it to adsorb surfactants and other cleaners so as to permit controlled application to the desired surface. The powder is useful in contact lens cleaners, facial scrubs, heavy-duty hand cleaners, automotive or household cleaners, vinyl or leather cleaners, tile and sanitary ware cleaners and the like. It may also be used as lubricants or as an additive in lubricants.

Moreover, these polymeric particles can be used as carriers for active agents such as drugs, pheromones, pesticides, insect repellants, herbicides, and fungacides, and also for cosmetics and perfumes and the like.

The following examples are presented for purposes of illustration and should not be construed as limiting the invention which is delineated in the claims.

The following test procedures were used to determine various properties of the polymers prepared in the Examples.

Procedure for Determining Total Adsorption Capacity (TAC)

A glass column, having a height of 110 mm and a diameter of 5 mm, made from a disposable capillary pipet and being sealed by glass wool at the bottom, was filled with approximately 0.05 grams of dry powder polymeric particles as prepared in the Examples. The top of the column was then sealed with glass wool. The bottom part of the column (conically-shaped) was connected to a "U"-shaped glass tubing, containing the liquid tested, and the column was immersed into a constant temperature bath. The liquid was allowed to enter the column slowly by gravity from the bottom to the top of the column, and left in the column for 5 minutes. The column was then disconnected from the tube and the liquid was sucked out of the column using a vacuum. The total adsorption capacity was calculated from the weight difference of the powder with the liquid and the dry powder according to the equation:

$$TAC\ (\%) = \frac{(\text{wt. powder} + \text{liquid}) - (\text{initial wt. powder})}{(\text{wt. powder} + \text{liquid})} \times 100\%$$

Blind experiment for adsorption on the glass wool and walls of the column was deducted. The determination was done at 25° C. for all liquids except glycerine, which was done at 90° C.

Procedure for Determining Free Flowing Capacity (FF)

Free Flowing Capacity is the maximum percent liquid added while still maintaining the powder in the free flowing state. The free flowing adsorption capacity was determined by addition of incremental amount of liquid to a known amounts of powder, using gentle mixing, until the powder was no longer free flowing. All determinations were completed at 25° C. except when glycerine was used, which determinations were carried out at 90° C. The capacity (FF) as shown in Table I was determined by the following calculation:

$$FF\ (\%) = \frac{(\text{wt. powder} + \text{liquid}) - (\text{initial wt. powder})}{(\text{wt. powder} + \text{liquid})} \times 100\%$$

Procedure for Determining Apparent Density

A graduated cylinder was filled with a known weight of the powder and the corresponding volume was determined after gently tapping the sides of the cylinder.

Procedure for Determining Dispersibility

A sample of the powder with an excess of the liquid are shaken and observed for miscibility.

EXAMPLES

EXAMPLES 1–21

In a three-necked resin reaction flask, 20 grams of the monomer in Table I were dissolved, at room temperature in 80 grams of isopropyl alcohol (or other solvent, if indicated) containing 0.4 grams of dibenzoyl peroxide. The solution was purged with nitrogen for 10 minutes, and a slow nitrogen stream was kept during the entire reaction time. Under stirring, 0.4 grams of p-dimethylamino benzoic acid, 2-ethylhexyl ester were added. After five minutes, the stirring was stopped. Usually a slightly exothermic polymerization occurred, the temperature rising to 50° to 60° C., and, then, the polymer began to precipitate. After cessation of the exotherm, the system was heated to 60° C. for 6 hours, and the contents of the flask solidified. If the reaction did not start at room temperature, the solution was heated to 30°–40° C. to initiate polymerization. After cooling to room temperature, the powder was washed with isopropyl alcohol (or other solvent, as indicated) and dried at room temperature or in vacuo, yielding 19.2 grams or 96% of theoretical.

TABLE I

| Example No. | Composition | Solvent | Adsorption Capacity & Free Flowing Capacity (%) | | | | | | | | | | | | Dispersibility in Solvent[a] | | | | Apparent Density g/cm³ |
|---|---|---|---|---|---|---|---|---|---|---|---|---|---|---|---|---|---|---|---|
| | | | Water | | Min. Oil | | Glycerine | | W171[b] | | D.C.344[c] | | Water | Triton X-100[d] 1:100 In Water | Mineral Oil | Silicone Oil D.C.344[c] | |
| | | | TAC[e] | Ff[f] | TAC | FF | TAC | FF | TAC | FF | TAC | FF | | | | | |
| 1 | Ethylene Glycol Dimethacrylate | IPA[g] | 54.5 | 54.5 | 84.8 | 61.5 | 79.2 | 70.6 | 84.9 | 64.3 | 81.5 | 68.8 | ± | + | ± | + | 0.0799 |
| 2 | Tetra-Ethylene Glycol Dimethacrylate | IPA | 78.3 | 73.7 | 73.7 | 64.3 | 83.9 | 72.2 | 83.9 | 73.7 | 79.2 | 71.4 | + | + | ± | + | 0.1534 |
| 3 | 1,6 Hexanediol Diacrylate | IPA | 72.2 | 61.5 | 70.6 | 58.3 | 80.8 | 70.6 | 74.3 | 66.7 | 64.3 | 61.5 | − | + | ± | + | 0.0508 |
| 4 | 1,6 Hexanediol Dimethacrylate | IPA | 44.4 | 37.5 | 81.5 | 70.6 | 66.7 | 64.3 | 91.7 | 73.7 | 80 | 75 | − | + | − | + | 0.0964 |
| 5 | Trimethylol Propanetri-Acrylate | IPA | 76.2 | 73.6 | 72.2 | 64.8 | 83.3 | 75 | 76.2 | 72.2 | 66.7 | 64.3 | ± | + | ± | + | 0.1282 |
| 6 | Ethoxylated Bisphenol A Bis Methacrylate | IPA | 37.5 | 37.5 | 64.3 | 61.5 | 64.3 | 64.3 | 66.7 | 64.3 | 75 | 69.3 | − | + | + | + | 0.1328 |
| 7 | Divinyl-Benzene | IPA | zero | zero | 90.4 | 66.7 | 76.2 | 70.6 | 87.5 | 66.7 | 80.8 | 72.2 | − | + | + | + | 0.0485 |
| 8 | Trimethylol Propane Tri-Methacrylate | IPA | 70.6 | 58.3 | 85.3 | 68.8 | 81.8 | 72.2 | 79.5 | 73.7 | 69.2 | 61.5 | − | + | + | + | 0.1276 |
| 9 | Pentaerithritol Tetra Methacrylate | IPA | 77 | 66.7 | 70.1 | 66.7 | 82.5 | 68.8 | 78.8 | 68.8 | 70.9 | 68.8 | + | + | + | + | 0.1654 |
| 10 | 1,3 Butanediol Dimethacrylate | IPA | 67.8 | 60 | 79.4 | 74 | 79.3 | 73.6 | 80.1 | 75.5 | 81.5 | 73.7 | − | + | − | + | 0.116 |
| 11 | 1,4 Butanediol Dimethacrylate | IPA | 88.2 | 73.7 | 82.3 | 76.2 | 82.3 | 75.2 | 82.1 | 75.5 | 88.5 | 76.1 | − | + | − | ± | 0.0790 |
| 12 | N,N'-Methylene bis-acrylamide | H₂O | 85.5 | 80 | 75.8 | 73.3 | 90.4 | 85 | 85.2 | 73.6 | 79.9 | 69.7 | + | + | − | + | 0.2618 |
| 13 | Diurethane[h] dimethacrylate | MEOH[i] | 61.7 | 54.8 | 72.4 | 58.8 | 84.1 | 71.8 | 75.5 | 62.9 | 64 | 58.5 | − | − | − | − | 0.1818 |
| 14 | N₂[j] | MEOH | 0 | 0 | 67 | 57.4 | 69.7 | 51.5 | 62 | 51.7 | 57.9 | 50.6 | − | − | − | + | 0.3361 |
| 15 | M₂D₂[k] | MEOH | 0 | 0 | 71.6 | 66.3 | 73.8 | 70.6 | 82 | 70.7 | 63.5 | 55.9 | − | − | − | − | 0.125 |
| 16 | M₂D₁₀[l] | ETOH[m] | 0 | 0 | 69.7 | 59 | 65.9 | 57.1 | 78.8 | 68.7 | 72.2 | 64.8 | − | − | − | − | 0.1364 |
| 17 | M₂D₂₅[o] | ETOH | 0 | 0 | 64 | 44.5 | 65 | 51.2 | 63.3 | 48.1 | 67.8 | 57.6 | − | − | − | − | 0.2143 |
| 18 | M₂D₁₈₀[p]/EGDMA[q] 10/90 weight % | IPA | 0 | 0 | 66.8 | 54 | 83.3 | 68.8 | 73.6 | 64.8 | 58.3 | 47.4 | − | + | − | − | 0.1440 |
| 19 | M₂D₁₈₀/EGDMA 20/80 weight % | IPA | 0 | 0 | 79.4 | 67.7 | 78.6 | 68 | 75.1 | 64.1 | 71.2 | 65.5 | − | + | − | − | 0.1043 |
| 20 | M₂D₁₈₀/EGDMA 40/60 weight % | IPA | 0 | 0 | 80.5 | 68.8 | 86.8 | 75.3 | 79.3 | 68 | 74.9 | 70.9 | − | − | − | − | 0.0727 |
| 21 | M₂D₁₈₀ | IPA | 0 | 0 | 64.8 | 59.2 | 51.7 | 37.3 | 63.8 | 54.9 | 66.2 | 60.6 | − | − | − | − | 0.3429 |

TABLE I-continued

| Example No. | Composition | Solvent | Adsorption Capacity & Free Flowing Capacity (%) | | | | | | | | | Dispersibility in Solvent[a] | | | | Apparent Density g/cm³ |
|---|---|---|---|---|---|---|---|---|---|---|---|---|---|---|---|---|
| | | | Water | | Min. Oil | | Glycerine | | W171[b] | | D.C.344[c] | | Water | Triton X-100[d] 1:100 In Water | Mineral Oil | Silicone Oil D.C.344[c] | |
| | | | TAC[e] | FF[f] | TAC | FF | TAC | FF | TAC | FF | TAC | FF | | | | | |
| | 60/40 weight % | | | | | | | | | | | | | | | | |

[a] + = complete
± = partial
− = sedimentation observed
[b] Wickenol (R) 171 (2-ethylhexyl oxystearate) available from Wicken Products, Inc. of Huguenot, New York.
[c] Dow Corning (R) 344 (a polydimethylcyclosiloxane fluid having a viscosity of 2.5 cst at 25° C.) available from Dow Corning Corporation, Midland, Michigan.
[d] Triton (R) X 100 (oxtylphenoxy ethoxy ethanol) available from Rohm & Haas Company, Inc., Philadelphia, Pennsylvania
[e] Total Adsorptive Capacity (%)
[f] Free Flowing Capacity (%)
[g] isopropyl alcohol
[h] 7,7,9-trimethyl-4,13-dioxo-3,14-dioxa-5,12-diazahexadecan-1,16-diol-dimethacrylate
[i] methylalcohol
[j] 1,4 bismethacryloyloxybuyltetramethyldisiloxane:

$$\underset{H}{\overset{H}{C}}=\underset{O}{\overset{O}{C}}-O-\underset{}{CH_2CH_2CH_2CH_2}-\underset{CH_3}{\overset{CH_3}{Si}}-O-\left[\underset{CH_3}{\overset{CH_3}{SiO}}\right]_n-\underset{CH_3}{\overset{CH_3}{Si}}-CH_2CH_2CH_2CH_2-O-\underset{O}{\overset{O}{C}}-\underset{H}{\overset{}{C}}=\underset{}{\overset{H}{C}}$$

where n = 0
[k] see j above, where n = 2
[l] see j above, where n = 10
[m] ethylalcohol
[o] see j above, where n = 25
[p] see j above, where n = 180
[q] ethylene glycol dimethacrylate

EXAMPLES 22–23

Free Flowing capacity for various pheromones, pesticides and their mixtures was determined. Some of the results are given in Table II.

TABLE II

| Example No. | Active Agent Composition | Free Flowing Capacity (%) | | |
|---|---|---|---|---|
| | | NALED[a] | TRIMEDLURE[b] | CUELURE[c] 99% NALED 1% |
| 22 | Tetraethylene Glycol Dimethacrylate | 77.4 | 69.08 | 65.34 |
| 23 | 1,6 Hexane Diol Dimethacrylate | 78 | 70.93 | 70 |

[a]NALED: dimethyl-1,2-dibromo-2,2-dichloroethylphosphate
[b]TRIMEDLURE: tert-butyl 4 (or 5)-chloro-methyl cyclo-hexane carboxylate
[c]CUELURE: 2-butanone-4(p-hydroxy phenyl)acetate

EXAMPLE 24

Similarly following examples 22 and 23, pheromones were entrapped in concentrations of more than 65% in polymers made from tetraethylene glycol dimethacrylate and 1,6 hexane diol dimethacrylate. Said phermones consisted of GOSSYPLURE (isomers of 7,11-hexadecadienylacetate); GRANDLURE (isomers of dimethyl-Δ-∞-cyclohexane acetaldehyde and alcohol; methyl eugenol; oriental fruit moth pheromone (9-dedecenyl acetate and alcohol); Z8,E8 dodecenyl acetate and alcohol; Z,11 hexadecenal aldehyde and alcohol; Z/E-11 tetradecenyl acetate; DISPARLURE (cis-7,8-epoxymethyl octadecane); alpha pinene; MUSCALURE (Z9 TRICOSENE); and apple maggot pheromone (hexyl acetate, butyl-2 methyl butanoate, propyl hexanoate, hexyl propanoate, butyl hexanoate, hexyl butanoate).

EXAMPLE 25

The following pesticides were entrapped in concentrations of more than 65% in polymers made from tetraethylene glycol dimethacrylate and 1,6 hexane diol dimethacrylate. The pesticides consisted of TEMASEPT (2,4 dibromo salicyl 4'bromoanilide); SPB 1382 (5 benzyl-3-furyl) methyl-2,2-dimethyl-3 (2 methyl propenyl cyclopropane carboxylate); Dimethoate (0,0-dimethyl-S-(n-methyl carbamoyl methyl) phosphorodithionate); ETHOPROP (S,S dipropyl-0-ethyl phosphodithionate); NNDD (N,N dimethyl dodecyl amine); DEET (N,N diethyl m-toluamide); TINACTIN (N-methyl N-(3-tolyl) thiono carbamate); SUMITHRIN (3-phenoxy-benzyl-d-cis trans chrysantemate); DIAZINON (0,0 diethyl-0-(2-isopropyl-4-methyl) thiophosphate); OMITE (2-(4-(1,1 dimethyl ethyl) phenoxy) cyclohexyl 2-propynyl sulfite); PHORATE (0,0-diethyl-s-[(ethyl thio) methyl] phosphoro dithionate); MALATHION (0,0-dimethyl-s-(1,2 dicarbethoxyethyl) dithionate); DDVP (2,2 dichlorovinyl dimethyl phosphate); D-TRANS-ALLETHRIN (d-1-2-allyl-4-hydroxy-3-methyl-2-cyclopenten-1-one ester of d-trans chrysanthemum monocarboxylic acid); METHOPRENE (isopropyl (2E-4E)-11-methoxy-3,7,11-trimethyl-2,4 dodecadienoate); PYRETHRINS; CHLORPYRIFOS (0,0-diethyl-0-(3,5,6 trichloro-2 pyridyl) phosphonthionate); OXIRANE (2,2 dimethyl-3-(3 methyl-5 (4-methyl ethyl-phenoxy) 3 pentenyl) oxirane); and IRGASAN DP 300 (2,4,4'trichloro-2'hydroxy diphenyl oxide).

These and other variations of the present invention may be made which fall within the scope of the appended claims even though such variations were not specifically discussed above.

That which is claimed is:

1. A method of forming an adsorptive polymer by precipitation polymerization, comprising the steps of:

(a) homogeneously mixing a solution of from about 0.1 to less than 25 parts by weight of a monomer consisting exclusively of one or more types of polyunsaturated monomers, from greater than 75 to about 99.9 parts by weight of a monomer solvent, wherein the total parts of said monomers and said monomer solvent is 100 parts, and between about 0.05 to 5 weight percent free radical initiator based on the weight of said monomer, (b) polymerizing said monomers by precipitation polymerization to form a polymer which is a combined system of particles, said particles ranging in size from 0.1 to 0.5 microns in diameter, and wherein said monomer solvent is a solvent for said monomers and a non-swelling non-solvent for said polymer, and (c) removing said solvent from said polymer to form a dry powder.

2. A method as claimed in claim 1 wherein said monomer is present from 2 parts by weight to less than 25 parts by weight and said solvent is present from greater than 75 parts by weight to 98 parts by weight.

3. A method as claimed in claim 1 wherein said monomer is present from 5 parts by weight to 20 parts by weight and said solvent is present from 80 parts by weight to 95 parts by weight.

4. A method as claimed in claim 1 wherein said removing step is by filtering and evaporating.

5. A method as claimed in claim 1 wherein said solvent has a boiling point of less than 80° C. at one atmosphere.

6. A method as claimed in claim 5 wherein said solvent is water-miscible.

7. A method as claimed in claim 6 wherein said solvent is isopropyl alcohol.

8. A method of forming poly(tetraethylene glycol methacrylate), comprising:

(a) homogeneously mixing a solution consisting essentially of from about 0.1 parts by weight to less than about 25 parts by weight of tetraethylene glycol dimethacrylate, from greater than about 75 parts by weight to about 99.9 parts by weight of anhydrous isopropyl alcohol, wherein the total weight of the tetraethylene glycol dimethacrylate and the anhydrous isopropyl alcohol is 100 parts, and 0.05 to 5 weight percent initiator based on the weight of the tetraethylene glycol dimethacrylate, (b) polymerizing the tetraethylene glycol dimethacrylate to form a polymer, and (c) evaporating the isopropyl alcohol from the polymer in an anhydrous atmosphere.

* * * * *